United States Patent [19]

Togawa et al.

[11] 4,049,524
[45] Sept. 20, 1977

[54] OXYGEN SENSOR WITH NONCATALYTIC ELECTRODE

[75] Inventors: Kimmochi Togawa, Yokohama; Hiroshi Takao, Kamakura; Kazuo Matoba; Katsuhiro Kishida, both of Yokohama, all of Japan

[73] Assignee: Nissan Motor Company, Limited, Japan

[21] Appl. No.: 701,185

[22] Filed: June 30, 1976

[30] Foreign Application Priority Data

July 8, 1975   Japan ................................. 50-83088

[51] Int. Cl.² ..................... G01N 27/30; G01N 27/46
[52] U.S. Cl. ................... 204/195 S; 204/294
[58] Field of Search .................. 204/195 S, 1 S, 294; 324/29

[56] References Cited

U.S. PATENT DOCUMENTS

| | | |
|---|---|---|
| 3,403,090 | 9/1968 | Tajiri et al. ........................ 204/195 S |
| 3,891,512 | 6/1975 | Jackson ............................... 204/1 S |
| 3,941,673 | 3/1976 | Takao et al. ....................... 204/195 S |

*Primary Examiner*—G. L. Kaplan
*Attorney, Agent, or Firm*—Robert E. Burns; Emmanuel J. Lobato; Bruce L. Adams

[57] ABSTRACT

In an oxygen sensor having a solid electrolyte layer such as stabilized zirconia and two electrode layers form respectively on both sides of the electrolyte layer, at least one electrode which is to be exposed to a gas mixture subject to measurement is made of carbon silicide to avoid catalyzing oxidation reactions, optionally with the addition of a minor amount of trisilicon tetranitride as a binder. The sensor features an exact and noticeable dependence of its output voltage on the oxygen concentration in a gas mixture in a non-equilibrated state as typified by an engine exhaust gas.

10 Claims, 3 Drawing Figures

OXYGEN SENSOR WITH NONCATALYTIC ELECTRODE

BACKGROUND OF THE INVENTION

This invention relates to oxygen sensor for detecting oxygen concentration in a gas mixture such as exhaust gas of an internal combustion engine. The sensor is of the concentration cell type comprising an ion conductive solid electrolyte layer provided with an electrode layer on each side, and the invention particularly relates to the electrode layer.

In an internal combustion engine, the air to fuel ratio of an air-fuel mixture consumed in the combustion chambers of the engine significantly affects both the efficiencies of the engine and the composition of the exhaust gas. Accordingly some of recent internal combustion engines, particularly automotive engines, are provided with a feedback control system for precisely controlling the air/fuel ratio of a combustible mixture fed to the engine based on a certain characteristic of the exhaust gas. In such a control system, the concentration of oxygen in the exhaust gas is usually taken as an indication of an actual air/fuel ratio of the combustible mixture and is detected with an oxygen sensor.

A typical oxygen sensor now in practical use is fundamentally an oxygen concentration cell which consists essentially of a layer of a solid electrolyte whose conductivity is predominantly attributable to the migration of oxygen ions and two electrode layers formed respectively on the front and rear surfaces of the electrolyte layer. When a gas mixture such as an engine exhaust gas is present on one side of the cell and a reference gas such as air on the other side, the electromotive force of the cell depends on the ratio of the oxygen partial pressure of the reference gas to that of the gas mixture.

Various oxide ceramics exemplified by $ZrO_2$, $ThO_2$ and $Bi_2O_3$ are known as solid oxygen-ion electrolyte materials. These oxides are usually used in the form of a solid solution with a stabilizing oxide such as e.g., CaO, $Y_2O_3$ or $Nb_2O_5$. Typical examples of commonly used solid solution systems are $ZrO_2$—CaO, $ZrO_2$—$Y_2O_3$, $Bi_2O_3$—$Nb_2O_5$ and $Bi_2O_3$—$4_2O_3$. The stabilizing oxide is usually contained in an amount of from about 5 to about 20 mol%.

The electrode layers are formed individually as a microporous coating which is in intimate contact with the surface of the electrolyte layer. The two electrode layers, which are made of either the same material or different ones, must be electronically conductive to serve as charge collectors. Besides, the electrode layers must be physically and thermochemically stable at elevated temperatures since oxygen sensors of the described type are in many cases used in a high temperature atmosphere ranging from about 500° C to about 1400° C. By reason of these fundamental requirements, a noble metal, particularly platinum, is commonly used as the material, at least as the conductive component of the material, of the electrode layers.

When an oxygen sensor of the described type is used for measuring the oxygen concentration in a gas mixture which contains oxygen and oxidizable gases and is in a non-equilibrated state as is typified by exhaust gas of an internal combustion engine, there arises a problem that a platinum electrode layer of the sensor catalyzes oxidation reactions between oxygen gas and the oxidizable gases contained in the gas mixture. As the result, the oxygen concentration in the gas mixture is measured nearly, if not exactly, in an equilibrated state, and hence the output of the oxygen sensor fails to indicate an actual oxygen concentration in the gas mixture in the original or non-equilibrated state. In connection with a catalytic action of the platinum electrode layer, the described oxygen sensor exhibits a unique output characteristic when the sensor is used in exhaust gas of an internal combustion engine to estimate the air/fuel ratio of a combustible mixture consumed in the engine from the output voltage of the sensor. The output voltage is on a relatively high level when the air/fuel ratio is below a stoichiometric ratio but on a clearly different and very low level when the air/fuel ratio is above the stoichiometric ratio. A great and sharp transition of the output voltage from the high level to the low level, or vice versa, occurs when the air/fuel ratio is around the stoichiometric ratio, so that it is very easy to judge whether the air/fuel ratio is above or below the stoichiometric ratio. However, the output voltages exhibits only a very small change so long as the air/fuel ratio remains on one side, either a higher side or a lower side, of the stoichiometric ratio. Accordingly, it is very difficult to numerically estimate the air/fuel ratio from the output voltage of the sensor exposed to the exhaust gas when the air/fuel ratio is deviated from the stoichiometric ratio. The use of costly platinum is an additional disadvantage of the above described oxygen sensor.

It has been tried to use a metal which is not a noble metal and exhibits no catalytic action on the oxidation reactions of, for example, hydrocarbons and carbon monoxide as the material of the electrode layers of the oxygen sensor. However, such a metal readily reacts with oxygen contained in a gas mixture to be measured at high temperatures. The original non-equilibrated stage of the gas mixture, therefore, is no longer retained when the gas mixture comes into contact with the surface of the electrolyte layer, and accordingly the output voltage of the sensor does not accurately correspond to the original or real oxygen concentration in the gas mixture.

It is an object of the present invention to provide an improved oxygen sensor which is identical with a conventional oxygen sensor of the concentration cell type in its solid electrolyte layer of a stable and noncatalytic material formed on one side of the electrolyte layer to be exposed to a gas mixture subject to measurement.

It is another object of the invention to provide an oxygen sensor of the concentration cell type whose output voltage upon exposure to exhaust gas of an internal combustion engine has a close relation to the air/fuel ratio of a combustible mixture consumed in the engine over a wide range of the air/fuel ratio.

An oxygen sensor according to the inventon has a layer of a solid oxygen-ion electrolyte typified by a stabilized zirconia, a first electrode layer formed on one side of the electrolyte layer to be exposed to a gas subject to measurement and a second electrode layer formed on the opposite side of the electrolyte layer to be exposed to a reference gas. Both the first and second electrode layers are permeable to gas. The sensor is of a known construction in these respects. According to the invention, the first electrode layer is made of a material comprising carbon silicide as a sole conductive component thereof.

The material of the first electrode material may consist of carbon silicide alone but may alternatively contain a minor amount of, usually in the range from about 1 to about 10 Wt% of carbon silicide, trisilicon tetranitride.

The second electrode layer is made of either the same material as the first electrode layer or a commonly used material such as, e.g., platinum.

BRIEF DESCRIPTION OF THE DRAWINGS

The invention will be fully understood from the following detailed description of a preferred embodiment with reference to the accompanying drawings, wherein.

DESCRIPTION OF THE PREFERRED EMBODIMENTS

Figure 1:
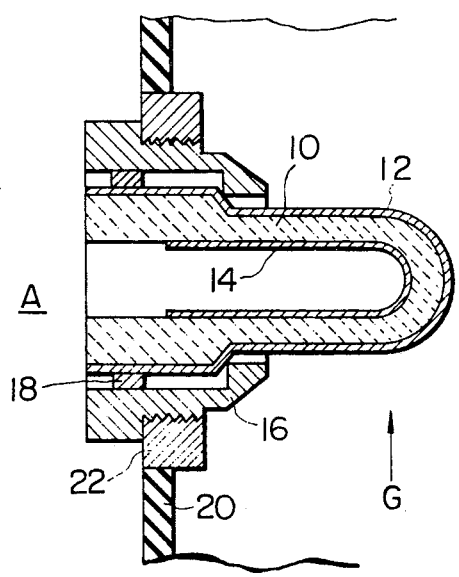
FIG. 1 is a longitudinal and sectional view of an oxygen sensor according to the invention.

An oxygen sensor shown in FIG. 1 is similar in general construction to a conventional oxygen sensor for use in the exhaust line of an internal combustion engine. In this embodiment, a solid electrolyte layer 10 has a tubular shape with a closed end. Alternatively, the electrolyte layer 10 may have the shape of a disc installed in a tubular housing having an opening to expose one side of the disc. The material of the solid electrolyte tube 10 is selected from the oxide ceramic materials which are described hereinbefore and exemplified by a $ZrO_2$—CaO system. An outer electrode layer 12 is formed as a porous coating on the outer surface of the solid electrolyte tube 10, and another porous electrode layer 14 is formed on the inner surface of the same tube 10. As is usual in conventional oxygen sensors of the same type, the outer and inner electrode layers 12 and 14 are formed preferably to entirely cover the closed end region of the tube 10. A housing 16 receives therein the electrolyte tube 10 with the provision of a retainer ring 18 such that the closed end of the tube 10 and hence the outer electrode layer 12 protrudes from the housing 16. The thus constructed oxygen sensor is attached to an exhaust pipe 20 of an internal combustion engine by the use of a threaded boss member 22, so that the outer electrode layer 12 is exposed to a flow of the exhaust gas indicated by the arrow G of the engine. The interior of the electrolyte 10, i.e. the inner electrode 14, is isolated from the exhaust gas G and is exposed to air A which serves as a reference gas.

The invention particularly relates to the material of the outer electrode layer 12 as will be described hereinafter more in detail. The inner electrode layer 14 is not of particular concern in this invention. The material of the inner electrode 14 may be the same as that of the outer electrode layer 12 but may alternatively be selected from commonly used materials exemplified by platinum, gold, silver, and alloys and mixtures containing one or more of these noble metals.

We have discovered that carbon silicide SiC (which is commonly called silicon carbide) serves as an excellent material of the outer electrode layer 12. Carbon silicide is electronically conductive to a degree sufficient to serve as a charge collector material but exhibits no catalytic action on oxidation reactions of various substances. Besides, carbon silicide is stable in oxygen-containing gases such as air and an engine exhaust gas up to a temperature of about 1450° C. The outer electrode layer 12 may be made of carbon silicide alone. It is permissible, however, to add a minor amount of an additive which is noncatalytic and serves as a binder for augmentation of the toughness of the electrode layer 12. The most preferable additive or binder is trisilicon tetranitride $Si_3N_4$. The amount of trisilicon tetranitride, when used, is preferably in the range from about 1 to about 10% by weight of carbon silicide.

The outer electrode 12 is formed to have a thickness in the range from 1 to 100 μm. If the thickness is less than 1 μm, the electrode layer 12 has an unfavorably high electrical resistance. On the other hand, the outer electrode layer 12 is liable to separate from the surface of the electrolyte tube 10 if formed more than 100 μm thick. Preferably, the outer electrode layer 12 has a thickness in the range from about 4 to about 20 μm.

A method of forming the outer electrode layer 12 and the output characteristic of an oxygen sensor according to the invention in an engine exhaust gas will be illustrated by the following examples.

EXAMPLE 1

The solid electrolyte tube 10 was a stabilized zirconia, $ZrO_2$(85 mol%)—CaO(15 mol%). Finely powdered SiC (the particle size was smaller than 1 μm) was uniformly suspended in a 0.1 Wt% aqueous solution of carboxymethylcellulose (CMC). The viscosity of this suspension was adjusted to 90 centipoises. Then the electrolyte tube 10 was partly immersed in this suspension in order to wet a portion of the outer surface of the tube 10 including the closed end region with the suspension, without wetting the inner surface of the tube 10. After withdrawal of the wetted tube 10 from the suspension, the wetted tube was fired at 1400° C in air for 1 hr. The thus formed outer electrode layer 12 was of practically pure SiC since CMC dissolved in the suspension coated on the outer surface of the tube 10 was burnt up by the firing procedure. The thickness of the outer electrode layer 12 was about 10 μm.

The inner electrode layer 14 was formed by coating the inner surface of the tube 10 with a paste containing finely powdered Pt and the firing the tube 10 at 1350° C in air for 1 hr.

The oxygen sensor of this example was attached to the exhaust pipe of a conventional automotive gasoline engine as illustrated in FIG. 1 to examine the relationship between the output voltage of the sensor exposed to the exhaust gas of the engine and the air/fuel ratio of an air-gasoline mixture fed to the engine. The result of the examination is presented in FIG. 3 as the curve (I) of the graph. The air/fuel ratio on the abscissa is given by weight, so that the stoichiometric ratio is about 14.8.

Figure 2:
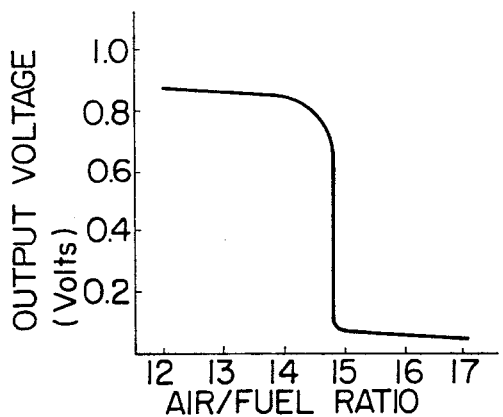
FIG. 2 is a graph showing an output characteristic of a conventional oxygen sensor when exposed to exhaust gas of an internal combustion engine.

For comparison, the output characteristic in the above described exhaust gas of a conventional oxygen sensor, which was produced generally in accordance with Example 1 except that the outer electrode layer 12 was formed identically with the inner electrode layer 14 of Pt, is presented by the graph of FIG. 2. As described hereinbefore, the dependence of the output voltage of this sensor on the air/fuel ratio of the combustible mixture is rather indistinct except when the air/fuel ratio is near the stoichiometric ratio.

In the sensor of Example 1, the output voltage continued to decrease noticeably as the air/fuel ratio increased, and the rate of decrease in the output voltage did not greatly depend on the air/fuel ratio. These features of the output characteristic of this sensor indicate that the outer electrode layer 12 of SiC exhibits no catalytic action and that the output voltage of this sensor greatly and exactly depend on the concentration of oxygen in the exhaust gas.

EXAMPLE 2

This example was generally similar to Example 1 except that finely powdered $Si_3N_4$ (the particle size was smaller than 1 μm) was mixed with the powdered SiC to amount to 5 Wt% of SiC before the preparation of the suspension.

Figure 3:
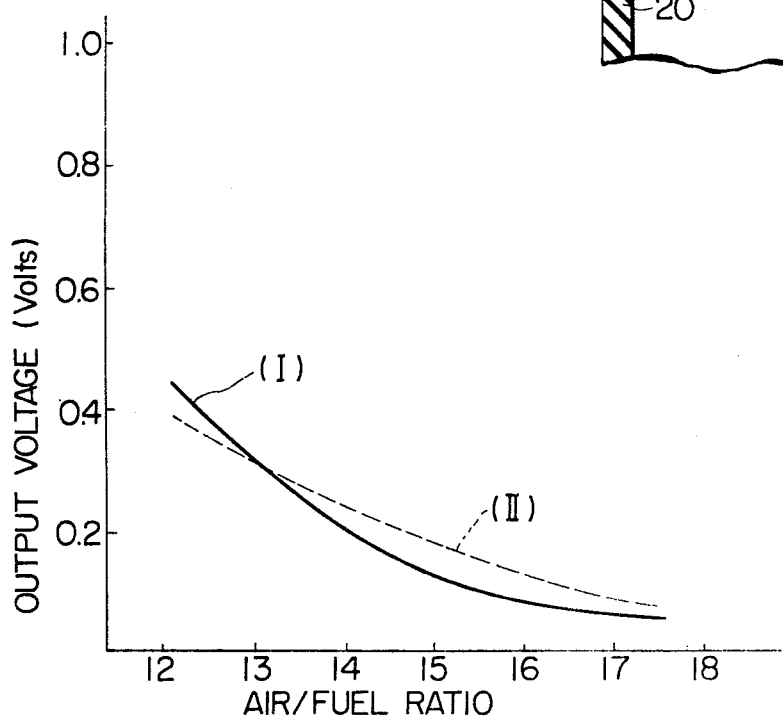
FIG. 3 is a graph showing an output characteristic of an oxygen sensor according to the invention when exposed to the same exhaust gas.

The curve (II) in FIG. 3 represents the output characteristic of the sensor of Example 2 examined under the same condition as in Example 1.

As demonstrated by these examples, an oxygen sensor according to the invention is particularly suitable for use in the exhaust line of an internal combustion engine for the purpose of accurately detecting the air/fuel ratio of a combustible mixture fed to the engine by measuring the oxygen concentration in the exhaust gas. In addition, the occurrence of misfire in the engine, if there is, can be sensed surely and quickly by an abrupt and noticeable change in the output voltage of this oxygen sensor.

What is claimed is:

1. In an oxygen sensor for sensing the difference in oxygen concentration between two gases, the sensor having a layer of solid oxygen-ion electrolyte, a first electrode layer formed on one side of the electrolyte layer to be exposed to a gas subject to measurement and a second electrode layer formed on the opposite side of the electrode layer to be exposed to a reference gas, both the first and second electrode layers being permeable to gas, the improvement comprising said first electrode layer being made of a material comprising carbon silicide as a sole conductive component thereof.

2. An oxygen sensor as claimed in claim 1, wherein said first electrode layer has a thickness in the range from 1 to 100 μm.

3. An oxygen sensor as claimed in claim 2, wherein said thickness is in the range from about 4 to about 20 μm.

4. An oxygen sensor as claimed in claim 2, wherein said material of said first electrode layer is carbon silicide.

5. An oxygen sensor as claimed in claim 2, wherein said material consists of a major amount of carbon silicide and a minor amount of trisilicon tetranitride as a binder.

6. An oxygen sensor as claimed in claim 5, wherein the amount of said trisilicon tetranitride is in the range from about 1 to 10% by weight of said carbon silicide.

7. An oxygen sensor as claimed in claim 2, wherein said solid oxygen-ion electrolyte is a solid solution of $ZrO_2$ and CaO.

8. An oxygen sensor as claimed in claim 2, wherein said second electrode layer is made of platinum.

9. An oxygen sensor as claimed in claim 8, wherein said electrolyte layer has the shape of a tube with a closed end, said first electrode layer being formed on the outer side of said electrolyte layer.

10. An oxygen sensor as claimed in claim 9, wherein said first electrode layer is formed to cover said closed end.

* * * * *